United States Patent [19]

Gotcher et al.

[11] 4,121,001

[45] Oct. 17, 1978

[54] CROSSLINKING AGENT FOR POLYMERS AND WIRE CONSTRUCTION UTILIZING CROSSLINKED POLYMERS

[75] Inventors: Alan J. Gotcher, Sunnyvale; Paul B. Germeraad, Palo Alto; Viktors Jansons, Los Gatos, all of Calif.

[73] Assignee: Raychem Corporation, Menlo Park, Calif.

[21] Appl. No.: 759,473

[22] Filed: Jan. 14, 1977

[51] Int. Cl.$^2$ .................. B32B 15/00; H01B 7/00; C08F 2/46
[52] U.S. Cl. .................. 428/35; 174/1105 R; 174/110 FC; 204/159.17; 204/159.19; 204/159.2; 428/36; 428/379; 428/421; 526/17; 526/18; 526/50
[58] Field of Search .................. 428/35, 36, 379, 421, 428/422, 411; 174/1105 R, 1105 FC; 526/17, 18, 50; 204/159.17, 159.18, 159.19, 159.2

[56] References Cited

U.S. PATENT DOCUMENTS

| | | | |
|---|---|---|---|
| 3,763,222 | 10/1973 | Aronoff et al. | 526/284 |
| 3,840,619 | 10/1974 | Aronoff et al. | 260/878 R |
| 3,894,118 | 7/1975 | Arnoff et al. | 526/249 |
| 3,911,192 | 10/1975 | Aronoff et al. | 427/44 |
| 3,968,015 | 7/1976 | Nyberg | 204/159.19 |
| 3,970,770 | 7/1976 | Dhami | 260/878 R |
| 3,985,716 | 10/1976 | Dhami | 260/875 |
| 3,995,091 | 11/1976 | Dhami | 428/379 |

Primary Examiner—William R. Dixon, Jr.
Attorney, Agent, or Firm—Lyon & Lyon

[57] ABSTRACT

A composition comprising a polymer having a processing temperature of at least 200° and from about 0.1 wt % up to about 30 wt % of crosslinking agent said crosslinking agent comprising a compound of the formula

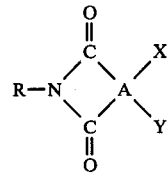

wherein X is hydrogen and Y is

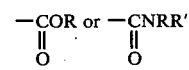

and X and Y are substituents on adjacent carbon atoms of A or wherein X and Y together form the imide ring system

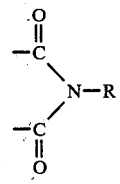

which is joined to A on adjacent carbons atoms, thereof, wherein A is an aromatic, heteroaromatic, alicyclic, or heterocyclic system or an open chain aliphatic moiety, where R is vinyl, allyl, methallyl or propargyl and wherein R' is hydrogen, $C_1$ to $C_{12}$ alkyl or R and mixtures thereof.

Compounds per se and articles manufactured from the above-indicated polymer compositon are also taught.

26 Claims, No Drawings

CROSSLINKING AGENT FOR POLYMERS AND WIRE CONSTRUCTION UTILIZING CROSSLINKED POLYMERS

BACKGROUND OF THE INVENTION

A large number of high melting fluorocarbon polymers possess a combination of mechanical, dielectric and chemical properties which make them particularly useful as electrical insulation materials. In order to maximize utilization of these fluorocarbon polymers under high temperature or overload conditions, crosslinking of the fluorocarbon polymers is required. Crosslinking of high temperature resistant fluorocarbon polymers is particularly difficult since the polymers are normally processed at temperatures which are too high for most chemical crosslinking agents. As an alternative to chemical crosslinking, irradiation crosslinking of these polymers has been tried. However, to achieve a suitable level of crosslinking without degradation, it is necessary to add a crosslinking agent or coreactant to the fluorocarbon polymers, a so-called "prorad".

The prior art teaches the existence of a variety of prorads. See for example U.S. Pat. Nos. 3,970,770, 3,985,716, 3,911,192, 3,894,118, 3,840,619, 3,763,222 and 3,995,091.

However, all of these prior art crosslinking agents suffer from one or more shortcomings in comparison with the crosslinking agents of the present invention.

DESCRIPTION OF THE INVENTION

This invention relates to certain imide containing compounds which are novel compositions of matter. This invention also relates to polymeric compositions comprising high processing temperature polymers, especially fluorocarbon polymers, containing one or more imide containing crosslinking agents (prorads) including inter alia the aforesaid novel compositions of matter. This invention also relates to wire insulated with, and cable jacketed with, the aforesaid polymeric compositions in crosslinked form.

The prorads of the present invention are particularly useful for enhancing the crosslinking of fluorocarbon polymers which are processed, that is, extruded and/or molded at temperatures of 200° or greater, especially 250° or greater. Additionally, the crosslinking agents of the present invention improve the elevated temperature mechanical properties of the crosslinked polymers, especially elevated temperature elongation, abrasion and deformation resistance. Fluorocarbon polymers with which the crosslinking agents of the present invention may advantageously be utilized include homopolymers, copolymers and terpolymers such as ethylene-tetrafluoroethylene copolymers, ethylene-chlorotrifluoroethylene copolymers, polyvinylidene fluoride homopolymers, tetrafluoroethylenevinylidene fluoride copolymers, tetrafluoroethylene-hexafluoropropylene copolymers, vinylidene fluoride hexafluoropropylene copolymers, vinylidene fluoride hexafluoropropylene tetrafluoroethylene terpolymers and the like. Mixtures of any of the above enumerated polymers may also be advantageously crosslinked using the crosslinking agents of the present invention.

The crosslinking agents of the present invention are suitably present in the polymer in an amount ranging from 0.1 to 30 weight percent, but will normally be employed in the range of 1-10 percent by weight. The polymer or polymers and crosslinking agents are blended, that is processed in the melt at an elevated temperature for a period of time sufficient to melt-process, but insufficient to crosslink. Ths mixture is then formed as desired, cooled to ambient temperature, and the formed cooled article irradiated to effect crosslinking of the polymer.

The crosslinking agents of the present invention can, if desired, be utilized in conjunction with one or more of the crosslinking agents taught by the prior art, especially those taught in U.S. Pat. Nos. 3,970,770, 3,985,716, 3,911,192, 3,894,118, 3,840,619, 3,763,222 and 3,995,091.

When a composition, according to the present invention, is employed as an insulation coating, as for example, on wire, the composition is extruded by conventional techniques directly onto the surface of the conductor, preferably as a relatively thin wall coating. Thereafter, the extruded composition, while on the surface of the conductor, is subjected to a dose of radiation sufficient to provide the desired degree of crosslinking without substantially degrading the material. It has been determined that a radiation dose in the range of about 1–40 megarads, and preferably about 3–20 megarads, most preferably 5–10 megarads, is suitable to provide the desired degree of crosslinking.

Additional adjuvants such as fillers including silica and carbon black, stabilizers, antioxidants, coloring agents and additional plasticizers and/or crosslinking agents may suitably be incorporated into the fluorocarbon polymers in addition to the crosslinking agents of the present invention.

The crosslinking agents of the present invention comprise compounds of the following generic formula

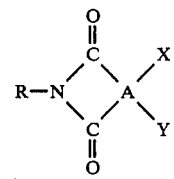

wherein X = hydrogen and Y =

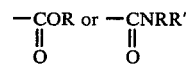

on adjacent carbons of A or wherein X and Y together form the ring system shown below:

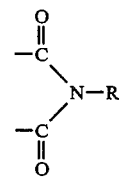

which is joined to moiety A on adjacent carbon atoms thereof, wherein R is vinyl, allyl, methallyl, or propargyl, where R' is hydrogen, $C_1$ to $C_{12}$ alkyl or R and wherein A is an aromatic, heteroaromatic, alicyclic, or heterocyclic ring system or an open chain aliphatic moiety. The following list is representative of a few starting materials suitable to provide moiety A:

1,2,4,5-benzenetetracarboxylic acid ethylene tetracarboxylic acid
ethane-1,1,2,2-tetracarboxylic acid
decahydronapthalene-1,4,5,8-tetracarboxylic acid
4,8-dimethyl-1,2,3,5,6,7-hexahydronapthalene-1,2,5,6-tetracarboxylic acid
cyclopentane-1,2,3,4-tetracarboxylic acid
pyrrolidine-2,3,4,5-tetracarboxylic acid
pyrazine-2,3,5,6-tetracarboxylic acid
butane-1,2,3,4-tetracarboxylic acid
cyclobutane-1,2,3,4-tetracarboxylic acid
thiophene-2,3,4,5-tetracarboxylic acid
furan-1,2,3,4-tetracarboxylic acid
cyclohexane-1,2,3,4,5,6-hexacarboxylic acid
cyclohexa-3,5-diene-1,2-dicarboxylic acid
bicyclo[2.2.2]oct-7-ene-2,3,5,6-tetracarboxylic acid
1,4-dimethyl-7,8-diphenyl-bicyclo[2.2.2]oct-7-ene-2,3,5,6-tetracarboxylic acid
1,4,7,8-tetrachloro-bicyclo[2.2.2]oct -7-ene-2,3,5,6-tetracarboxylic acid
1,8-dimethyl-bicyclo[2.2.2]oct-7-ene-2,3,5,6-tetracarboxylic acid
3,4-dicarboxy-1,2,3,4-tetrahydro-1-naphthalene-succinic dianhydride
thianthrenetetracarboxylic acid-5,5,10,10-tetroxide
1,3-bis-(3,4-dicarboxyphenyl)hexafluoropropane dianhydride
1,2,4-benzenetricarboxylic anhydride The preferred compounds of the present invention have the following structural formulae:

pounds comprehended by the formulae I through VIII are believed to be unknown to the art.

Although, as heretofore indicated, a wide variety of prima facie suitable radiation crosslinking agents (prorads) for fluorocarbon polymers are known to the prior art, all such known materials pose problems when the polymer must be processed at a high temperature, e.g., greater than 200°, especially greater than 250°, prior to being subjected to irradiation. Conventionally, the polymer plus prorad plus other additives (e.g., fillers, antioxidants, etc.) are blended together a homogeneously as possible and then formed, as by molding or extrusion such as extrusion coating of conductor to form a jacketed wire. The formed article, e.g., the jacketed wire, is then irradiated to crosslink the polymer insulation. Unfortunately, some of the most desirable polymers from a general property standpoint require relatively high temperatures (e.g., in excess of 250°) for effective extrusion or molding. Subjecting most of the prior art prorads to such temperatures causes severe problems, i.e., much of the prorad is lost through evaporation and/or the prorad undergoes thermally induced homopolymerization or degradation. In either case the prorad is no longer available to effect radiation induced crosslinking of the polymer. Also, where thermally induced homopolymerization has occurred, this prorad homopolymer is present as an undesirable and frequently marginally stable impurity. The compounds of the present invention are uniquely superior in having both a low volatility and a limited tendency to homopolymerize when

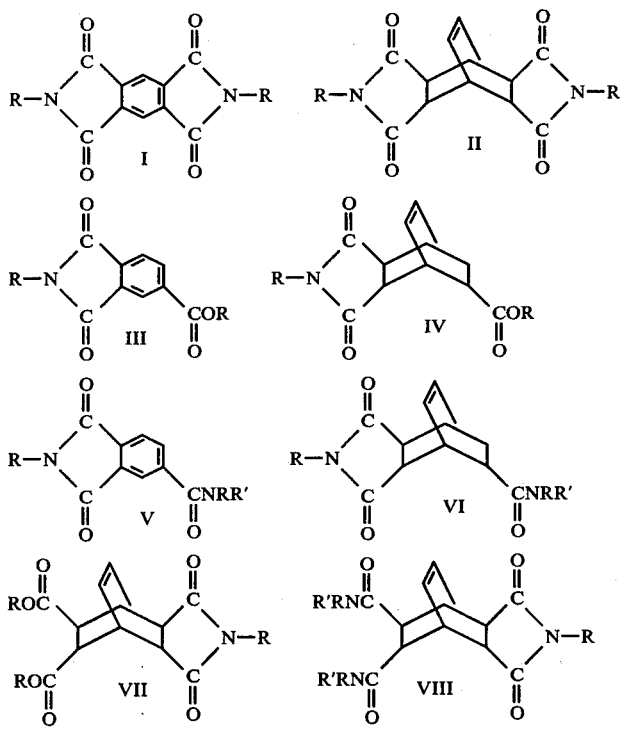

Compound I wherein R is allyl is taught by the prior art (Chem. Abstr. 73, 36098, Akiyama et.al, Japan 70 09,547) as coreacting with N-ethylmaleimide to afford a thermoset resin; similarly, compound III wherein R is allyl has been reported to be useful as a monomer for the synthesis of heat resistant resins (Chem. Abstr. 78, 135895b, Hara, Japan 73 05,586). All the other comsubjected to temperatures even in excess of 250°. They are, however, highly effective as crosslinking agents for fluorocarbon polymers when subjected to ionizing radiation. The compounds of the present invention are therefore particularly useful for high melting fluorocarbon polymers such as polyvinylidene fluoride (e.g., Pennwalt Kynar), ethylene chlorotrifluoroethylene copolymers (e.g., Allied Chemical Halar), and ethylenetetrafluoroethylene copolymers (e.g., duPont Tefzel).

The crosslinking agents of the present invention are made by efficient and economical synthetic routes:

To form compounds I and II the dianhydride of moiety A, that is the compounds

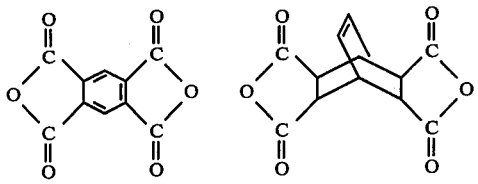

when A is a benzene or bicyclooctene ring system, respectively, are reacted with at least twice as many moles of $RNH_2$ wherein R is allyl, methallyl, or propargyl. Compounds I and II are diimides and the preparation thereof is by synthetic methods generally known, per se. That is, the reaction of dianhydrides with two or more molar equivalents of an amine to form a diimide is well known.

The preparation of Compounds III, IV, V and VI is effected by a similar reaction sequence. The compounds

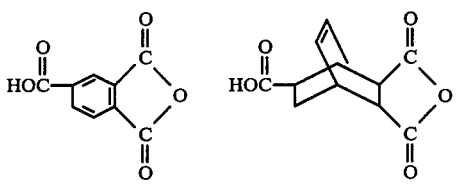

are reacted with $RNH_2$, preferably in molar excess, to afford (using for illustrative purposes A = phenyl):

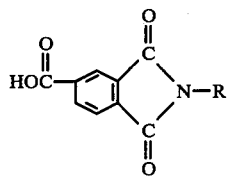

This intermediate is further reacted with, for example, $PCl_5$ or $SOCl_2$ to afford the corresponding acid chloride

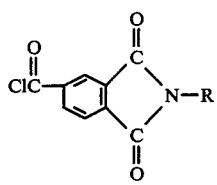

which is then reacted with at least one mole of ROH or RR'NH to afford:

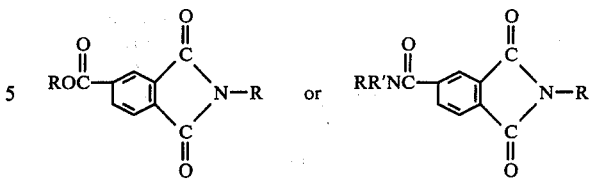

Where it is desired that R be a vinyl group it is not possible to prepare the compounds of the invention directly using ROH or $RNH_2$ since these compounds are not stable. Alternative synthetic methods are available such as formation of the unsubstituted vinyl ester anhydride which is then reacted with allylamine to give the desired ester imide. A similar synthetic sequence is suitable for other A moieties.

Of course, mixtures of amines and/or alcohols and/or anhydrides can be used to form the compounds of the present invention, or instead or likewise, mixtures of all or any of said compounds can be incorporated into the fluorocarbon polymer to serve as the crosslinking agent.

Although the previous description of this invention has been stated in terms of crosslinking fluorocarbon polymers, it should be understood that the compounds of the present invention are also useful to effect or enhance the radiation crosslinking of other polymers including halogenated polymers such as polyvinyl chloride and polyvinylidene chloride, polyolefins such as polyethylene, polypropylene and ethylene-propylene copolymers, copolymers and terpolymers of ethylene with other olefinic monomers such as vinyl acetate and ethyl acrylate, high performance polymers such as polyarylene ether ketone (e.g., Raychem Stilan), polyarylene ether sulfone (e.g., Union Carbide Udel or Radel), polyphenylene oxide (e.g., General Electric PPO), polyesters such as polyoxybenzoate (e.g., Carborundum Exxel) and polybutylene terephthalate (e.g., Eastman Tenite), polyamides (e.g., Dynamit Nobel Trogamid), polycarbonates (e.g., General Electric Lexan), and high performance thermoplastic elastomers such as polyester ether block copolymers (e.g., duPont Hytrel) and polyurethane ether block copolymers. The conditions of radiation and amount of prorad used in such polymers are substantially the same as for the fluorocarbon polymers. It should be noted that the compounds of the present invention can under certain circumstances be advantageously used in conjunction with other prorads to effect or enhance the radiation crosslinking of polymers. In addition, the compounds of the present invention, mixtures thereof, or mixtures thereof with from about 5 to 50 wt % of other prior art prorads, have been found to plasticize polymers, especially at elevated temperatures such as the polymer processing temperature. It is apparent to those skilled in the art that the degree of plasticization is dependent upon the amount of prorad introduced into the polymer formulation, that is, higher levels of prorad impart substantially greater levels of plasticization to the polymer as to allow a reduction to be made in the processing temperature of the polymer composition. These compositions can thereafter be crosslinked to impart superior mechanical properties to the end product.

This invention is further illustrated by examples which serve to illustrate specific details, aspects and embodiments of the invention. All parts are by weight unles otherwise indicated. All temperatures throughout the specification and claims are in degrees centigrade. All tests unless otherwise indicated were carried out at 23°. The term melting point or crystalline melting point is defined as that temperature at which the last traces of crystallinity as measured by differential scanning calorimetry is observed. The polymer processing temperature as that term is used herein is defined as a temperature above the crystalline melting point of any polymeric component at which temperature the polymer melt has a viscosity of not more than $2 \times 10^6$ poise. The majority of polymeric components useful in the practice of the present invention, however, have melt viscosities of less than $10^5$ poise at the processing temperature. The term wire can connote either bared conductor or jacketed conductor as is apparent from the context.

Certain of the tests utilized are first described.

MODULUS MEASUREMENT

To determine the relative level of crosslinking in these polymeric resins, a modulus test conducted at 320° was used because conventional methods to determine crosslinking levels by gel analysis require the polymer to be soluble. In the case of ethylene tetrafluoroethylene copolymers, there are no known solvents below 200°. This modulus test measures the stress required to elongate a resin by 100% at a temperature of 320°. High values obtained from this test indicate increasing resistance to elastic deformation or development of a significant amount of a three-dimensional network. The 320° temperature was chosen as it is intermediate between the decomposition temperature (~350°) and the crystalline melting point (~280°) for ethylene tetrafluoroethylene copolymers. The modulus measurement expressed as the $M_{100}$ value can be calculated by:

$$M_{100} = \frac{\text{stress in pounds to elongate sample by 100\%}}{\text{initial cross-sectional area in square inches}}$$

Should the sample rupture prior to 100% elongation, the $M_{100}$ is calculated using the equation:

$$M_{100} = \frac{\left(\frac{\text{stress in pounds to elongate sample to break}}{\text{elongation at rupture}}\right)}{\text{initial cross-sectional area in inches}}$$

CUT THROUGH TEST

A sample of the wire is placed between an anvil and a 90° included angle wedge shaped weighted knife blade having a 5 mil flat at the knife edge. The anvil is hung by means of a stirrup from the load cell of an Instron tensile tester and the knife blade mounted on the movable bar of said tensile tester also by a stirrup so that the blade edge lies transversely over the wire specimen. The knife edge is advanced towards the wire conductor at a speed of 0.2 in per minute. Failure occurs when the knife edge contacts the conductor. The resulting electrical contact causes the tensile tester to stop advancing the blade. The peak reading from the load cell is taken to be the cut through resistance of the wire. This cut through test is not to be confused with a cut through test identified by Bowers et al., IEC Product R&D 1, 89 (1962). The latter test simulates an accelerated creep test in which the viscoelastic flow of a polymeric resin is altered by radiation crosslinking. Further information pertaining to enhancement of polymer creep resistance through crosslinking can be found in "Mechanical Properties of Polymers and Composites," by L. E. Nielsen, Vol. 1, p. 87, 1974.

EXAMPLE I

To a stirred slurry of 49.6 parts of bicyclo[2.2.2]oct-7-ene-2,3,5,6-tetracarboxylic-2,3:5,6-dianhydride in 200 parts of glacial acetic acid was added dropwise with cooling (ice bath) 26.2 parts of allylamine over a period of 5–10 min. The reaction mixture was gradually heated and held at reflux for 30 min, resulting in a clear amber solution. Upon cooling, a crystalline material precipitated, was collected by filtration and was recrystallized from toluene to give 58.5 parts (90%) of colorless crystals: mp 202°–3°. Thinlayer chromatography indicated one compound ($SiO_2/CHCl_3$ as eluent). Nuclear magnetic resonance and infrared spectral analysis confirmed the formation of the desired diimide: nmr: $\delta(CDCl_3)$ ppm, 2.9–3.2 (multiplet, 4H, —CH—C̲H̲—C=O), 3.6–3.9 (multiplet, 2H, —C̲H̲—CH—C=O), 4.05 (doublet, 4H, —C̲H̲$_2$—CH=CH$_2$). 4.9–6.0 (multiplet, 6H, —CH$_2$—CH=CH$_2$), 6.15 (triplet, 2H, —CH—C̲H̲=C̲H̲—CH—); ir: (KBr)cm$^{-1}$, 3130 (w) and 3020 (m) [unsat. CH], 1770 (s) and 1705 (vs) [imide—C=O].

EXAMPLE II

A sample of N,N'-di-(2-propenyl)-1,2,4,6-benzenetetracarboxylic-1,2:4,5-diimide was prepared by a reaction analogous to that of Example I from 1,2,4,5-benzenetetracarboxylic-1,2:4,5-dianhydride and allylamine (93% yield): colorless crystals, mp 222.5°–223.5°. The material was shown to be one compound by thinlayer chromatography. Its identity was established by nuclear magnetic resonance and infrared spectral analysis: nmr: $\delta(CDCl_3)$ ppm, 4.35 (doublet, 4H, —N—C̲H̲$_2$—CH=CH$_2$), 5.0–6.3 (multiplet, 6H, —CH$_2$—CH=CH$_2$), 8.25 (singlet, 2H, aromatic hydrogen); ir:($\overline{KBr}$) cm$^{-1}$, 3120 (m, aromatic H), 2950 (w, aliphatic H), 1765 (s) and 1710 (vs) [imide —C=O].

EXAMPLE III

A sample of 2-propenyl 2,3-dihydro-1,3-dioxo-1H-2-(2-propenyl)isoindole-5-carboxylate was prepared in a three-step sequence: 1,2,4-benzenetricarboxylic anhydride (57.6 parts) was treated in the same manner as in Example I with excess allylamine (37.7 parts) to give 2,3-dihydro-1,3-dioxo-1H-2-(2-propenyl)isoindole-5-carboxylic acid(47.4 parts); colorless crystals, mp 155°–7°. A sample of 27.3 parts of this material was refluxed in 50 parts of thionyl chloride which contained approximately 0.5 parts of dimethylformamide. After a reaction time of 1 hour excess thionyl chloride was removed by distillation to give a crystalline residue of 2,3-dihydro-1,3-dioxo-1H-2-(2-propenyl)-isoindole-5-carboxylic acid chloride. An aliquot of 5.0 parts of this material was dissolved in 10 parts of pyridine and 1.3 parts of allyl alcohol (excess) was added dropwise with stirring at room temperature. The resulting mixture was briefly heated to reflux, then cooled to room temperature followed by dilution with water to give a crystalline precipitate. Recrystallization first from aqueous acetic acid and then from methanol produced 3.6 parts of colorless crystals: mp 65°–6°. Thinlayer chromatography ($SiO_2/CHCl_3$ as eluent) indicated one single component. Nuclear magnetic resonance and infrared spectral analysis confirmed the identity of the desired 2-propenyl 2-3-dihydro-1,3-dioxo-1H-2-(2-propenyl)isoindole-5-carboxylate; nmr: $\delta$ ($CDCl_3$) ppm, 4.30 (doublet, 2H, N—C̲H̲$_2$—CH=CH$_2$), 4.90 (doublet, 2H, O—CH$_2$—CH=CH$_2$), 5.0–6.5 (multiplet, 6H, —CH$_2$—CH=CH$_2$), 7.85 (doublet, 1 H, aromatic hydrogen), 8.1–8.4 (multiplet, 2H aromatic hydrogen); ir (KBr) cm$^{-1}$, 3120 (w, aromatic H), 2950 (w, aliphatic H), 1770 (m) 1718 (vs) [imide and ester —C=O], 1280 (s, aromatic ester —C—O).

EXAMPLE IV

A sample of 2,3-dihydro-1,3-dioxo-1H-2-(2-propenyl)isoindole-5-carboxylic acid chloride (5 parts), whose preparation was described in Example III, was dissolved in 10 ml of pyridine, and 2.2 parts of diallylamine was added dropwise with stirring while cooling to maintain a reaction temperature of approximately 10°–15°. The resulting reaction mixture was heated briefly to reflux, and then cooled and poured into water. An oil separated which was taken up in ether and washed sequentially with aqueous hydrochloric acid, aqueous potassium carbonate, and water. The ethereal solution was then freed of colored impurities by treatment with charcoal and alumina, followed by evaporation to dryness to give 5.5 parts of a colorless oil. The material consisted of one compound as shown by thinlayer chromatography (SiO$_2$/CHCl$_3$ as eluent). Nuclear magnetic resonance and infrared spectral analysis confirmed the identity of the desired 2,3-dihydro-1,3-dioxo-1H-2-(2-propenyl)isoindole-5-(N,N-di-2-propenyl)carboxamide; nmr:δ(CDCl$_3$) ppm, 3.7–4.3 (multiplet, 4H, —N,N-amide—CH$_2$—CH=CH$_2$), 4.30 (doublet, 2H, N-imide-CH$_2$—CH=CH$_2$), 5.0–6.3 (multiplet, 6H, N,N-imide amide—CH$_2$—CH=CH$_2$), 7.7–8.0 (multiplet, 2–3H, aromatic hydrogen); ir:(neat) cm$^{-1}$, 1630–1640 (s) [secondary amide —C=O], 1710 (s) and 1770 (m) [imide —C=O].

EXAMPLE V

A sample of ethenyl 2,3-dihydro-1,3-dioxo-1H-(2-propenyl)isoindole-5-carboxylate was prepared in two steps: 4-carboethenoxy-1,2-benzenedicarboxylic anhydride was synthesized according to the procedure given in Organic Syntheses, Coll. Vol. IV, p. 977, from vinyl acetate and 1,2,4-benzenetricarboxylic anhydride by effecting a mercuric acetate catalyzed ester interchange. A pale yellow crystalline material was obtained: mp 123°–127°; nmr:δ(CDCl$_3$) ppm, 4.85 (quartet, 1H) and 5.20 (quartet, 1 H) [—CH=CH$_2$], 7.48 (quartet, 1 H, —CH=CH$_2$), 7.9–8.7 (multiplet, 3 H, aromatic hydrogen): ir; (Nujol) cm$^{-1}$, 1645 (w) [CHR=CH$_2$ stretch], 1730 (s) [ester —C=O], 1775 (s) and 1845 (m) [anhydride —C=O]. The above compound (21.8 parts) was dissolved in 175 parts of glacial acetic acid, and 5.7 parts of allylamine was added dropwise with stirring at room temperature. The reaction exotherm was controlled by cooling with water. After completing amine addition the reaction solution was concentrated to a volume of 125 parts by distillation of acetic acid. The resultant concentrate was allowed to cool to room temperature. A crystalline, colorless precipitate formed which was collected by filtration. Recrystallization from heptane produced 13.1 parts of colorless needles (mp 91.5°–93.0°). Thinlayer chromatography indicated one compound and a trace of non-moving impurity. A sample of 6.2 parts of this material was further purified by treatment with charcoal and alumina in chloroform solution. This process, after solvent removal, produced 6.0 parts of colorless crystals which consisted of one compound as shown by thinlayer chromatography (SiO$_2$/CHCl$_3$ as eluent). Nuclear magnetic resonance and infrared spectral analysis confirmed the identity of the desired ethenyl 2,3-dihydro-1,3-dioxo-1H-(2-propenyl)isoindole-5-carboxylate; nmr: δ(CDCl$_3$) ppm, 4.30 (doublet, 2H, —N—imide—CH$_2$—CH=CH$_2$), 4.6–5.1 (multiplet, 2H, —O—CH=CH$_2$), 5.2–6.2 (multiplet, 3H,—N—imide—CH$_2$—CH=CH$_2$), 7.38 (quartet, 1 H, —O—CH=CH$_2$), 7.85 (doublet, 1 H, aromatic H) 8.1–8.5 (multiplet, 2H, aromatic H); ir:(Nujol) cm$^{-1}$, 1645 (m) [CHR=CH$_2$ stretch], 1720 (s) [vinyl ester —C=O], 1735 (s) and 1770 (m) [imide —C=O].

EXAMPLE VI

As previously indicated, the compounds of the present invention possess a combination of properties which make them uniquely superior to prior art prorads. This and the following examples illustrate some of these advantages such as higher homopolymerization temperatures and lower volatility without comprising prorad response to ionizing radiation or compatibility with polymeric resins.

The temperature at which a variety of reported prior art fluorocarbon prorads, and also compounds according to the present invention commence thermally induced homopolymerization, was evaluated by differential scanning calorimetry. In all cases, the compounds were tested in a nitrogen atmosphere at a heating rate of 20°/minute from 50° to 400°. Results are reported in Table I.

Polymerization at 250° or below drastically reduces the usefulness of the prorad since exposure to temperatures above 250° is required to process many of the most useful fluorocarbon polymers. As is apparent from Table I, only three of the prior art compounds, viz., Compounds F, G and H had polymerization initiation temperatures above 250°. These results indicate that most prior art compounds, e.g., Compounds A–E, undergo significant homopolymerization during processing. This causes a significant reduction of crosslinking enhancement and leads to incorporation of undesirable prorad-homopolymer into the fluorocarbon host polymer.

TABLE I

| Compound | Structure | Polymerization Temp., ° |
|---|---|---|
| | Homopolymerization Temperatures of Selected Prorads | |
| A | CH$_2$=CH—CH$_2$—O—C(=O)—[C$_6$H$_4$]—S(=O)$_2$—[C$_6$H$_4$]—C(=O)—O—CH$_2$—CH=CH$_2$ | 210 |

TABLE I-continued
Homopolymerization Temperatures of Selected Prorads

| Compound | Structure | Polymerization Temp., ° |
|---|---|---|
| B | triazine with three allyloxy (O-CH$_2$-CH=CH$_2$) substituents | 220 |
| C | 1,3-phenylene-bis-maleimide | 230 |
| D | 1,3,5-triazine-2,4,6-trione (isocyanurate) with three N-CH$_2$-CH=CH$_2$ substituents | 250 |
| E | benzene-1,2,4-tricarboxylic acid tris(allyl) ester | 250 |
| F | benzene-1,3,5-tricarboxylic acid tris(allyl) ester | 260 |
| G | 4,4'-oxybis(benzoic acid) bis(allyl) ester | 260 |
| H | 1,1,3-trimethyl-3-phenylindane dicarboxylic acid bis(allyl) ester | 280 |
| I | N,N'-diallyl-pyromellitic diimide | 360 |
| II | N,N'-diallyl bicyclic diimide | 330 |
| III | allyl ester / N-allyl phthalimide compound | 260 |

EXAMPLE VII

The effectiveness of a prorad is dependent on its concentration in the host polymer during irradiation. Prorads of high volatility are expected to be lost, at least in part, during melt processing due to evaporation. To illustrate this point a variety of known prorads and several of the compounds of the instant invention were compared on the basis of volatility using thermogravimetric analysis at a heating rate of 20°/minute under a nitrogen atmosphere. The results are shown in Table II. Examination of these data reveals that the prior art compounds A, C, G, and H have volatility comparable to compounds of the instant invention, while all other prior art compounds manifest excessive volatility at 250°. However, these results are far from conclusive since prorad loss can result from homopolymerization and evaporation. Table III takes this factor into account by analyzing weight loss below the homopolymerization temperature. As is apparent from the data, the prorads of the present invention again show excellent results. However, under these experimental conditions which measure merely evaporative loss, only two of the known prorads, i.e., compounds A and H, demonstrate the comparably low volatility of the prorads of the instant invention, while the other prior art prorads show a significantly greater relative weight loss, by a factor of three or more, under identical conditions.

EXAMPLE VIII

Examination of the simultaneous effect of volatility and homopolymerization can be made by processing a standard formulation containing various prorads and comparing the resultant extrudates. The processability of prior art prorads is compared with prorads of the instant invention using a ¾ inch Brabender extruder, to produce a thin wall (10 mil) Tefzel (duPont, ethylene-tetrafluoroethylene copolymer) insulation on 20 AWG tin plated copper conductor. The results are given in Table IV.

As is apparent from this Table, only the prorads of the instant invention provide a commercially viable product. Prior art prorads each demonstrate to a degree after processing product discoloration, porosity, gelation, and surface imperfections. Each of these drawbacks magnifies the difficulty of extruding the thin wall wire insulation required of a high performance product.

Table IV

| | Processing Comparison of Several Prorads in a Standard Formulation | | | | | | |
|---|---|---|---|---|---|---|---|
| | Extrusion Temp. Profile, ° | | | | Extruded Insulation Properties | | |
| Compound | Zone 1 | Zone 2 | Zone 3 | Head | Color | Surface Appearance | Integrity |
| B | 265 | 310 | 330 | 330 | tan | v. rough | foamed |
| D | 265 | 310 | 330 | 330 | tan | v. rough | foamed |
| F | 245 | 295 | 330 | 340 | tan | rough | foamed |
| G | 265 | 310 | 335 | 345 | off white | lumps | good |
| H | 240 | 300 | 340 | 370 | off white | lumps | good |
| I | 240 | 300 | 340 | 380 | white | excellent | good |
| II | 240 | 300 | 340 | 370 | white | excellent | good |
| III | 265 | 300 | 340 | 370 | white | good | good |

4.0 Wt. % prorad concentration in Tefzel fluoropolymer for all samples at start of processing.

TABLE II

| Volatility of Selected Prorads by Thermal Gravimetric Analysis[1] | | | |
|---|---|---|---|
| | Weight % loss at | | |
| Compound | 200° | 250° | 300° |
| A | 0 | 1 | 4 |
| B | 15 | 91 | 100 |
| C | 2 | 5 | 12 |
| D | 22 | 95 | 100 |
| E | 3 | 14 | 54 |
| F | 2 | 7 | 37 |
| G | 1 | 5 | 24 |
| H | 0 | 2 | 7 |
| I | 0 | 4 | 23 |
| II | 0 | 1 | 6 |

[1]Heating rate of 20°/minute, $N_2$ atmosphere

TABLE III

| Volatility of Selected Prorads by Isothermal Weight Loss[1] | | | | |
|---|---|---|---|---|
| | Weight % loss after exposure time (min) | | | |
| Compound | 5 | 10 | 20 | 30 |
| A | 0.0 | 0.0 | 0.1 | 0.2 |
| B | 4.3 | 12.2 | 27.2 | 41.3 |
| C | 1.7 | 2.8 | 3.8 | 4.4 |
| D | 11.3 | 27.2 | 56.7 | 87.0 |
| E | 1.2 | 3.1 | 6.9 | 10.9 |
| F | 0.8 | 1.6 | 2.8 | 4.2 |
| G | 1.0 | 1.6 | 3.3 | 3.5 |
| H | 0.1 | 0.3 | 0.7 | 1.1 |
| I | 0.1 | 0.6 | 0.9 | 1.1 |
| II | 0.0 | 0.0 | 0.0 | 0.0 |

[1]Temperature = 175°, $N_2$ atmosphere

EXAMPLE IX

Each of the previous examples delineates parameters which influence the performance of a prorad containing polymer composition when subjected to thermal processing and subsequent ionizing radiation in order to effect crosslinking. The ultimate choice of a prorad is dictated by a combined consideration of processing behavior and end product performance. The significant overall advantages accruing from the use of prorads of the instant invention over those of the prior art was demonstrated by conducting appropriate test extrusions and product evaluations. Identical polymer formulations containing none or 5% of a prior art prorad or 5% of a prorad of the instant invention, were compared as a wire product after extrusion from a ¾ inch Brabender extruder to produce a thin wall (10 mil) insulation on 20 AWG tin plated copper conductor, followed by irradiation to 12 Mrads and annealing at 150° for 1 hour. These wire insulations were then subjected to identical analyses for comparison. The results are provided in Table V. Examination of these data clearly shows the advantages of the prorads of the instant invention, as demonstrated by superior processing behavior and significantly improved wire insulation properties. Comparison of the cut through resistance at room temperature and at elevated temperature shows an improvement greater than 50% over the best of the prior art prorad containing wire compositions.

terephthalate; polyurethane ester block copolymer, polyurethane ether block copolymer, polyesterether block copolymers or mixtures thereof.

TABLE V

Processing and Performance Evaluation of Prorad Formulations

| Compound | Tp[1] | Volatility[2] | Appearance | Crosslinking Density $M_{100}$, psi | Ultimate Elongation % | Cut Through Resistance 25° | 150° |
|---|---|---|---|---|---|---|---|
| None | N/A | N/A | Smooth, clear | melts | 160 | 24 | 3.9 |
| D | 250 | 50 | Badly foamed | | | | |
| E | 250 | 11 | Badly foamed | Extrudate integrity was inadequate for testing. | | | |
| F | 260 | 4 | Foamed | | | | |
| H | 280 | 1 | Uneven, contained gel particles | 97 | 102 | 29 | 4.1 |
| I | 360 | 1 | Smooth, yellow | 590 | 100 | 50 | 6.5 |
| II | 330 | 0 | Smooth, white | 220 | 130 | 42 | 6.3 |

[1] Polymerization temperature, °
[2] Volatility at 175° after 30 minutes, % weight loss.

We claim:

1. A composition comprising an organic crosslinkable polymer having a melt processing temperature of at least 200° and from about 0.1 wt % up to about 30 wt % of crosslinking agent said crosslinking agent comprising a compound of the formula

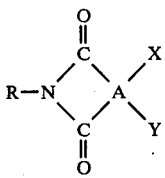

wherein X is hydrogen and Y is

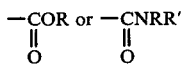

and X and Y are substituents on adjacent carbon atoms of A or wherein X and Y together form the imide ring system

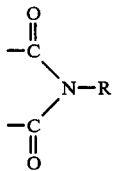

which is joined to A on adjacent carbons atoms, thereof, wherein A is an aromatic, heteroaromatic, alicyclic, or heterocyclic system or an open chain aliphatic moiety, where R is vinyl, allyl, methallyl or propargyl and wherein R' is hydrogen, $C_1$ to $C_{12}$ alkyl or R, or a mixture of said compounds.

2. A composition in accordance with claim 1 wherein said polymer comprises a fluorocarbon polymer.

3. A composition in accordance with claim 2 wherein said polymer comprises ethylene-tetrafluoroethylene copolymers and terpolymers, ethylenechlorotrifluoroethylene copolymers and terpolymer vinylidene fluoride polymers, tetrafluoroethylene-vinylidene fluoride copolymers, tetrafluoroethylene-hexafluoropropylene copolymers and vinylidene fluoride-hexafluoropropylene copolymers and mixtures thereof.

4. A composition in accordance with claim 1 wherein said polymer comprises a polyarylene ether ketone, polyarylene ether sulfone, polyphenylene oxide, polycarbonate, polyoxybenzoate, polyamide, polybutylene 5. A composition in accordance with claim 1 wherein said composition contains from about 5 to about 15 weight percent crosslinking agent.

6. The composition of claim 1 wherein the crosslinking agent is N,N'-di(2-propenyl)-bicyclo[2.2.2]oct-7-ene-2,3,5,6-tetracarboxylic-2,3:5,6-diimide.

7. The composition of claim 1 wherein the crosslinking agent is N,N'-di-(2-methyl-2-propenyl)-bicyclo[2.2.2]oct-7-ene-2,3,5,6-tetracarboxylic-2,3:5,6-diimide.

8. The composition of claim 1 wherein the crosslinking agent is N,N'-di-(2-propynyl)-bicyclo[2.2.2oct-7-ene-2,3,5,6-tetracarboxylic-2,3:5,6-diimide.

9. The composition of claim 1 wherein the crosslinking agent is N,N'-diethenyl-bicyclo[2.2.2]oct-7-ene-2,3,5,6-tetracarboxylic-2,3:5,6-diimide.

10. The composition of claim 1 wherein the crosslinking agent is N,N'-di-(2-propenyl)-1,2,4,5-benzenetetracarboxylic-1,2:4,5-diimide.

11. The composition of claim 1 wherein the crosslinking agent is 2-methyl-2-propenyl 2-(2-methyl-2-propenyl)-2,3-dihydro-1,3-dioxo-1H-isoindole-5-carboxylate.

12. The composition of claim 1 wherein the crosslinking agent is 2-propenyl 2(2-propenyl)-2,3-dihydro-1,3-dioxo-1H-isoindole-5-carboxylate.

13. A composition in accordance with claim 1 wherein said crosslinking agent contains about 5 to 50 wt percent of a compound selected from the group consisting of triallylcyanurate, triallylisocyanurate, triallyl trimellitate, triallyl trimesate, tetraallyl pyromellitate, diallyl-4-4'-oxydibenzoate, diallyl-4,4'-sulfonyldibenzoate and 2-propenyl 2,3-dihydro-3-[4-(2-propenoxycarbonyl)phenyl]-1,1,3-trimethyl-1H-indene-5-carboxylate.

14. The composition of claim 13 wherein said crosslinking agent comprises a mixture of N,N'-di-(2-propenyl)-bicyclo[2.2.2]oct-7-ene-2,3,5,6-tetracarboxylic-2,2:5,6-diimide and 1,3,5-tri-(2-propenyl)-s-triazine-2,4,6(1H, 3H, 5H)-trione.

15. The composition of claim 13 wherein said crosslinking agent comprises a mixture of N,N'-di(2-propenyl)-1,2,4,5-benzenetetracarboxylic-2,3:5,6-diimide and 1,3,5-tri-(2-propenyl)-s-triazine-2,4,6(1H, 3H, 5H)-trione.

16. The composition of claim 13 wherein said the crosslinking agent comprises a mixture of 2-propenyl 2,3-dihydro-1,3-dioxo-1H-2-(2-propenyl)-isoindole-5-carboxylate and 1,3,5-tri-(2-propenyl)-s-triazine-2,4,6(1H, 3H, 5H)-trione.

17. A formed article comprising an electrical conductor having as an insulating coating thereover the product of the process of crosslinking the composition of claim 1.

18. An article in accordance with claim 17 wherein said article has been subjected to ionizing radiation at a dose level of about 1 to 40 megarads to cause said crosslinking.

19. A shaped article comprising the composition of claim 1 in elongate substantially tubular form.

20. The article of claim 19 wherein the composition has been subjected to ionizing radiation at a dose level of about 1 to 40 megarads.

21. An injection molded hollow shaped article comprising the composition of claim 1.

22. The article of claim 21 wherein the composition has been subjected to ionizing radiation at a dose level of about 1 to 40 megarads.

23. A substantially planar extruded shaped article comprising the composition of claim 1.

24. The article of claim 23 wherein the composition has been subjected to ionizing radiation at a dose level of about 1 to 40 megarads.

25. The product of the process of crosslinking the composition of claim 1.

26. The product of claim 25 wherein said crosslinking is by exposure to ionizing radiation at a dose level of from about 1 to 40 megarads.

* * * * *